US009846146B2

(12) United States Patent
Noh et al.

(10) Patent No.: US 9,846,146 B2
(45) Date of Patent: Dec. 19, 2017

(54) HYDROGEN DETECTING SENSOR

(71) Applicants: Hyundai Motor Company, Seoul (KR); Ajou University Industry-Academic Cooperation Foundation, Suwon, Gyeonggi-do (KR)

(72) Inventors: Yong Gyu Noh, Gyeonggi-do (KR); Ho June Bae, Seoul (KR); Hyung Tak Seo, Seoul (KR); Yeong An Lee, Gyeongsangnam-do (KR); Shankara S. Kalanur, Gyeonggi-do (KR)

(73) Assignees: Hyundai Motor Company, Seoul (KR); Ajou University Industry-Academic Cooperation Foundation, Suwon, Gyeonggi-do (KR)

( * ) Notice: Subject to any disclaimer, the term of this patent is extended or adjusted under 35 U.S.C. 154(b) by 0 days.

(21) Appl. No.: 14/752,960

(22) Filed: Jun. 28, 2015

(65) Prior Publication Data
US 2016/0103107 A1 Apr. 14, 2016

(30) Foreign Application Priority Data
Oct. 8, 2014 (KR) .................. 10-2014-0136138

(51) Int. Cl.
*G01N 7/00* (2006.01)
*G01N 31/10* (2006.01)
*H01M 8/0444* (2016.01)

(52) U.S. Cl.
CPC .......... *G01N 31/10* (2013.01); *H01M 8/0444* (2013.01); *H01M 2250/20* (2013.01); *Y02E 60/324* (2013.01); *Y02P 70/56* (2015.11); *Y02T 90/32* (2013.01)

(58) Field of Classification Search
CPC ....................................................... G01N 7/00
USPC ............................. 422/83, 98, 86, 400, 500
See application file for complete search history.

(56) References Cited

U.S. PATENT DOCUMENTS

| 2002/0017126 A1* | 2/2002 | DiMeo, Jr. | ............. G01N 21/59 73/31.05 |
| 2002/0121370 A1* | 9/2002 | Kurkjian | ............... E21B 49/081 166/250.01 |
| 2007/0251822 A1 | 11/2007 | Hoagland et al. | |
| 2009/0137054 A1* | 5/2009 | Hoagland | ............. B82Y 30/00 436/102 |

(Continued)

FOREIGN PATENT DOCUMENTS

| KR | 10-2009-0115324 A | 11/2009 |
| KR | 10-2011-0120039 A | 11/2011 |

(Continued)

OTHER PUBLICATIONS

Hong, Eunpyo et al, "Heterostructured metal sulfide (ZnS-CuS-CdS) photocatalyst for high electron utilization in hydrogen production from solar water splitting", Jrl. of Industrial and Engineering Chemistry, 20 (2014) pp. 3869-3874.

*Primary Examiner* — Brian J Sines
(74) *Attorney, Agent, or Firm* — Mintz Levin Cohn Ferris Glovsky and Popeo, P.C.; Peter F. Corless

(57) ABSTRACT

Disclosed herein is a hydrogen detecting sensor that includes a sulfide-metal catalyst, such that hydrogen gas can be detected visibly with naked eyes. Particularly, the hydrogen detecting sensor includes a substrate, a sulfide layer formed on the substrate and chemically discolored when exposed to hydrogen, and a metal catalytic layer formed on the sulfide layer.

10 Claims, 7 Drawing Sheets

(56) References Cited

U.S. PATENT DOCUMENTS

| | | | |
|---|---|---|---|
| 2010/0059375 A1* | 3/2010 | Weiller | G01N 27/06 |
| | | | 204/433 |
| 2010/0290050 A1 | 11/2010 | Uchiyama | |
| 2011/0171066 A1 | 7/2011 | Captain et al. | |
| 2012/0188551 A1 | 7/2012 | Langhammar et al. | |
| 2013/0004372 A1 | 1/2013 | Roberson et al. | |
| 2015/0050745 A1 | 2/2015 | Karato et al. | |

FOREIGN PATENT DOCUMENTS

| | | |
|---|---|---|
| KR | 10-2012-0070160 A | 6/2012 |
| WO | 2013/129473 A1 | 7/2015 |

\* cited by examiner

HYDROGEN DETECTING SENSOR

CROSS-REFERENCE TO RELATED APPLICATION

This application is based on and claims the benefit of priority to Korean Patent Application No. 10-2014-0136138, filed on Oct. 8, 2014 in the Korean Intellectual Property Office, the disclosure of which is incorporated herein in its entirety by reference.

TECHNICAL FIELD

The present invention relates to a hydrogen detecting sensor. In particular, the hydrogen detecting sensor may include a sulfide-metal catalyst such that hydrogen can be detected visibly with naked eyes.

BACKGROUND

Recently, hydrogen fuel energy has been emerged as substitute energy source of fossil fuel, since the hydrogen fuel energy can be regenerated unlimitedly and does not produce environment pollution. Thus, research into storing and controlling hydrogen fuel energy has been actively conducted in various fields such as production technologies, storage technologies, and transportation and movement technologies. In particular, research into hydrogen fuel cell vehicles using hydrogen fuel energy have been on the rise.

Meanwhile, hydrogen fuel or hydrogen gas has a possibility of being ignited and exploded when concentration thereof in the air is greater than about 4% (vol/vol), and thus, a highly sensitive hydrogen sensor that can rapidly and accurately detect leakage of hydrogen gas may be considered as a core technology for commercialization of hydrogen fuel energy in various technical fields utilizing hydrogen fuel energy.

Conventionally, equipment of detecting hydrogen gas using catalytic, electrochemical, and mechanical factors, and principles related to acoustic waves, heat conductivity, change in resistance, and work functions has been used. However, the conventional detection equipment may be mostly large in size, high in price, and has a limitation in movement and application fields, and further, detection operation thereof may be performed at high risk in an environment with an explosion possibility.

In order to solve the above mentioned problem, a sensor employing an optical hydrogen detection scheme has been proposed. The sensor based on the optical hydrogen detection scheme may be available for remote detection using an optical cable and may not require an electric circuit in a detection region, thereby providing high stability. However, such a sensor based on the optical hydrogen detection scheme may use high-priced materials, thereby increasing manufacturing cost, and its corrosion due to oxygen and moisture in the air may cause degradation of sensitivity and shorten a lifespan.

Thus, a technique is demanded for manufacturing a highly efficient and stable hydrogen detection sensor that may be extensively used in the various industries, can be detectable by naked eyes, can be manufactured easily at reduced cost in a manufacturing process, and may not be degraded in sensitivity.

SUMMARY

In preferred aspects, the present invention may provide solutions to the above-mentioned problems.

In one aspect, provided is a hydrogen detecting sensor. The hydrogen detecting sensor may be recognized with naked eyes, reduce manufacturing cost, facilitate manufacturing processes, and provide excellent hydrogen detection efficiency.

According to an exemplary embodiment of the present invention, provided is a hydrogen detecting sensor based on a sulfide-metal catalyst. In particular, the hydrogen detecting sensor may include: a substrate; a sulfide layer formed on the substrate and discolored when exposed to hydrogen gas; and a metal catalytic layer formed on the sulfide layer. In a preferred aspect, the sulfide layer may be chemically discolored by a chemical reaction with the hydrogen gas.

Still further provided is a vehicle part that comprises the hydrogen detecting sensor as described herein. The hydrogen detecting sensor may be applied to all exemplary vehicle parts, which are related to hydrogen in fuel cell vehicles, such as a hydrogen storage tank, high pressure regulator, a tube having a joint, a valve for hydrogen gas, or a stack enclosure for a fuel cell, but not limited thereto.

Other aspects of the invention are disclosed infra.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
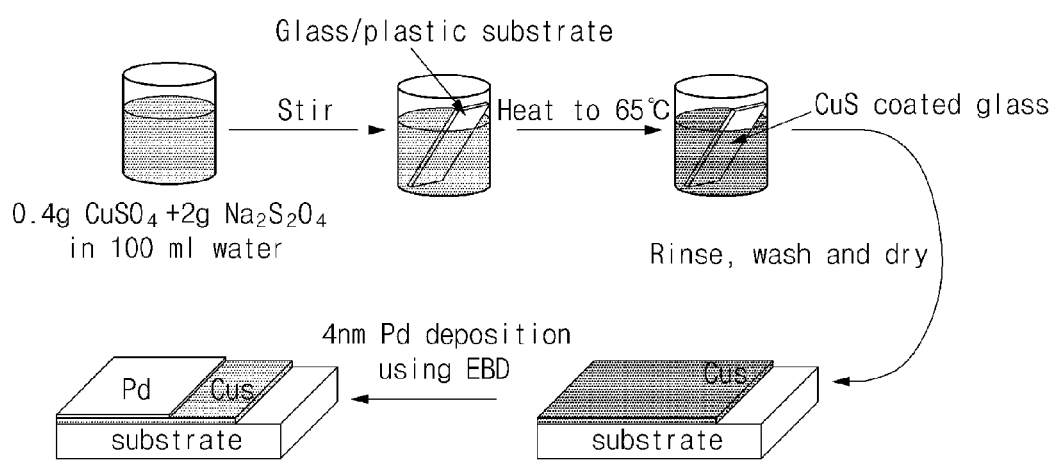
FIG. 1 is a schematic view illustrating an exemplary method for manufacturing an exemplary hydrogen detecting sensor using a hydrothermal method according to an exemplary embodiment of the present invention.

The terminology used herein is for the purpose of describing particular exemplary embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

Hereinafter, exemplary embodiments of the present invention will be described in detail with reference to the accompanying drawings. Here, terms or words used in the specification and claims should not be limited and construed as common or dictionary meanings, and should be construed as meanings and concepts according to the technical spirit of the present disclosure based on the principle that the inventor can appropriately define the concept of each term for describing the invention in the best way.

Until recently, materials such as $WO_3$ and $MoO_3$ have been used as chemochromic hydrogen sensor materials. A conventional hydrogen sensor including these materials and a metal catalytic layer may have reversible decoloration change, such that can be used repeatedly. Further, such materials may be used in various forms such as a coating agent, pigment, paint, ink, and the like and may detect low concentration of hydrogen gas. However, these materials mostly cost much and the metal catalytic layer may be readily corroded by oxygen contained therein and moisture from the atmospheric environment, thereby degrading sensitivity over time and shortening a lifespan. In order to prevent such disadvantages, an anti-moisture protective film may be added on the metal catalytic layer, which causes deterioration of detection efficiency.

In order to solve the above mentioned problems, the present invention provides a hydrogen detecting sensor using optical/chemical discoloration or coloration based on a sulfide-metal catalyst.

Accordingly, in an exemplary embodiment of the present invention, provided is a hydrogen detecting sensor that may include: a substrate; a sulfide layer formed on the substrate and chemically discolored when exposed to hydrogen; and a metal catalytic layer formed on the sulfide layer.

In the hydrogen detecting sensor, the substrate may be formed of a solid phase material supporting the sulfide layer. The solid phase material may not be particularly limited and may be flexibly selected by a person skilled in the related arts. Exemplary solid phase material may include glass, flexible plastic, silicon, quartz, fused silica, stainless steel, mica, carbon, carbon nano-tube, polymer, ceramic, or porcelain enamel, without limitation.

In the hydrogen detecting sensor of the present invention, the sulfide layer may include a discoloration material that may be discolored or chemically discolored when exposed to hydrogen. Such "discoloration or coloration" or "chemical discoloration/coloration" may be visibly observed by naked eyes on a surface of the discoloration material. In preferred embodiment, the "discoloration or coloration" or "chemical discoloration/coloration" may refer to a change in visibly detectable colors which is induced by chemical reaction such as reduction, oxidation and the like, with the hydrogen. That is, there would be a visible color change (as detected with naked eyes) of the sulfide layer between 1) before the sulfide layer is exposed to the hydrogen; and 2) at least about 1 second, about 5 seconds, about 10 seconds, about 20 seconds, about 30 seconds, about 40 seconds, about 50 seconds, or about 60 seconds after the sulfide layer is exposed to the hydrogen. Further, the "discoloration or coloration" or "chemical discoloration/coloration" may be visibly detected with naked eyes when the discoloration material in the sulfide layer in an amount of about 1 wt %, about 2%, about 3 wt %, about 4 wt %, about 5 wt %, about 7 wt %, about 10 wt %, about 15 wt %, about 20 wt %, about 25 wt %, about 30 wt %, about 35 wt %, about 40 wt %, about 50 wt %, about 60 wt %, about 70 wt %, about 80 wt %, about 90 wt %, about 99 wt %, or about 100 wt % based on the total weight thereof is chemically reacted with the hydrogen.

Exemplary discoloration materials to the hydrogen may be a sulfide that does not include oxygen, and may include at least one or more of sulfides selected from the group consisting of CdS, SnS, MoS, ZnS, SeS, FeS, PdS, and CuS (covellite). In particular, the discoloration material may be CuS.

The sulfide layer may be formed to have unique particular properties by selecting and adjusting appropriate experimental conditions. For instance, the sulfide layer may be deposited using a well-known chemical bath deposition (CBD) method or a dry deposition method, and in this case, the sulfide layer may be deposited to have a thickness ranging from about 40 nm to about 50 nm but the thickness may not be particularly limited. When the thickness is greater than about 50 nm, an amount of a metal catalyst or a thickness of the metal catalyst layer may be increased together proportionally.

According to an exemplary embodiment, when the sulfide layer is formed as a CuS thin film, the CuS thin film may be formed by the CBD method, such as a hydrothermal method. For example, the copper sulfate and sodium thiosulfate may react in a mole ratio of about 1:5 in an aqueous solution at a temperature of about 65° C. and thus prepared material may be deposited as shown in FIG. 1.

In particular, when the CBD method is performed at a low temperature equal to or less than about 70° C., a global substrate, for example, a glass substrate, a flexible substrate, a flexible plastic substrate, and the like, may be used.

The sulfide layer may be deposited on the entire regions of the substrate such that any surface of substrate may not be exposed.

The sulfide layer deposited on the substrate by the above described method, e.g. hydrothermal method, may have improved bonding characteristics with respect to the substrate, robustness, and stability, and thus, the sulfide layer may be prevented from being separated from the substrate.

For operating the hydrogen detecting sensor, hydrogen molecules may be decomposed by a catalytic reaction.

According to an exemplary embodiment, the hydrogen detecting sensor may include a metal catalytic layer on the sulfide layer.

The metal catalytic layer may include at least one or more substances of metal particles selected from the group consisting of palladium (Pd), platinum (Pt), ruthenium (Ru), manganese (Mn), nickel (Ni), and gold (Au). In particular, in the metal catalytic layer may include Pd or Pt metal catalytic particles that increase sensitivity of the hydrogen detecting sensor and significantly enhance durability thereof.

The thickness of the metal catalytic layer may vary according to the thickness of the sulfide. For example, a thickness ratio of CuS: Pd may be of about 40 to 50:4 to 5 in nanometer (nm), but the thickness range may not be particularly limited.

The metal catalytic layer may be deposited on a portion of the sulfide layer such that at least other portion of the sulfide layer may be exposed.

The metal catalytic layer may be formed by using hydrothermal method or e-beam evaporation (EBD).

For instance, the hydrothermal method may be performed by mixing $PdCl_2$ (palladium chloride) in a methanol or ethanol solvent and exposing the mixture to ultraviolet ray (dominant wavelength of about 365 nm, output of about 1000 W) for about two to three minutes. When the hydrothermal method is performed less than about two minutes, palladium may not be properly decomposed, and when the hydrothermal method is performed greater than about three minutes, the color of palladium may turn dark substantially such color change may not be detected visibly.

Alternatively, the EBD may be performed by irradiating electron beams with an acceleration voltage of about 7.0 kV and current of about 40 mA at room temperature, however such conditions may be varied based on the acceleration voltage and a state of equipment. For example, in case of deposition of about 4 nm, the EBD may be performed at a deposition rate of about 0.1 nm thickness per about 0.1 Å/s per second for about 9 to 10 minutes.

When the hydrogen detecting sensor according to an exemplary embodiment of the present invention manufactured thusly is exposed to a hydrogen gas, a hydrogen molecule may be dissociated to proton and electron by the metal catalytic layer (e.g., a sheet containing Pd metal catalyst), and the dissociated electron of the hydrogen atom may pass through the metal catalytic layer so as to be transmitted to the thin film of sulfide (e.g. CuS). As such, reduction of the sulfide layer may occur. For example, as bivalent Cu (II) of the CuS thin film may be reduced to monovalent Cu (I), chemical discoloration reaction that can be recognized with naked eyes may occur as shown in the following Reaction Formula I.

It has been reported that hydrogen, when bonded to cation and anion, may influence electrical and structural characteristics of a material. Meanwhile, due to van der Waals force, hydrogen may have qualitatively different behaviors depending on an introduced host. In other words, hydrogen may serve as either a doner ($H^+$) or receptor ($H^-$). Thus, in the hydrogen detecting sensor system, hydrogen may be bonded to $S^-$ species as shown in the following Reaction Formula I to mainly affect a valance band of the hydrogen detecting ensor system.

$Cu^{2+}S + e^- (\text{from } H_2) \rightarrow Cu^{+1}S$      [Reaction Formula I]

When the hydrogen detecting sensor according to an exemplary embodiment of the present invention is manufactured by the above described method and principle, the hydrogen detecting sensor may have a dark green color before being exposed to hydrogen gas. When the hydrogen detecting sensor is exposed to a hydrogen gas, the color may be changed to dark brown, thereby detecting the hydrogen gas. For example, in the presence of 100%(vol/vol) hydrogen gas, the color of the thin film may be completely changed in to dark brown, while with an amount of 1%(vol/vol) hydrogen gas, less color change may be observed. Further, a response time of the hydrogen detecting sensor according to an exemplary embodiment of the present invention may be less than about 20 seconds with the 100%(vol/vol) hydrogen gas, while in the presence of 1%(vol/vol) hydrogen gas, about one minute, starting from a point of time at which the hydrogen gas is allowed to pass therethrough, may be required.

The hydrogen detecting sensor according to an exemplary embodiment of the present invention may be utilized in an optical sensor and chemical coloring/discoloration. Further, themanufacturing cost thereof may be reduced, and the hydrogen detecting sensor may be easily formed in increased area.

When an oxide in the related art is used, chemical discoloration/coloration may occur due to reduction of an oxide by hydrogen, which causes a reversible reaction by oxygen in the air. However, according to exemplary embodiments of the present invention, hydrogen atom formed by the catalytic material may react with sulfur of a sulfide, regardless of oxygen, to form hydrogen sulfide ($H_2S$), thus being reduced. The reduced sulfide may be maintained in the air, rather than being recovered. Accordingly, the hydrogen detecting sensor system according to an exemplary embodiment of the present invention using a hydrogen ($H_2$) chemochromic effect that can be detected with naked eyes may relate to an irreversible reaction. Also, the hydrogen detecting sensor according to an exemplary embodiment of the present invention can measure hydrogen at a concentration of about 1% or less, e.g., about 0.8%, using an optical measurement scheme. In addition, the hydrogen detecting sensor according to an exemplary embodiment of the present invention may not require a protecting filter, a passivation layer, or the like, which may reduce sensitivity or selectivity, as reported in the related art. As such, the hydrogen detecting sensor may be utilized in various sensor application fields such as a coating agent, pigment, paint, and the like.

Specific exemplary embodiments have been described in the detailed description of the present disclosure. However, various modifications may be made without departing from the scope of the present disclosure. Technical concepts of the present disclosure should not be determined to be limited to the described exemplary embodiments of the present disclosure but be determined by claims and equivalents thereof, as well as claims.

EXAMPLE

Experiment Method and Equipment a. A discoloration and decoloration reaction of the hydrogen detecting sensor with respect to 100% hydrogen was made using a sealed gas chamber.

b. A discoloration reaction of about 1%(vol/vol) hydrogen gas (containing about 99% (vol/vol) nitrogen gas) was inspected under an atmosphere of a mixture of nitrogen gas, oxygen gas, and vapor by using an open chamber with an outlet.

c. Each gas coloration experiment was conducted at room temperature, and a flow rate of about 2 L/min was maintained on a sample.

d. Morphology and structural characteristics of a surface of a deposited thin film were measured using the scanning electron microscope (SEM) (Hitachi S4800, Japan) and transmission electron microscopy (TEM) (JEM-2100F, JEOL, USA).

e. Energy dispersed X-ray spectroscopy (EDS) was measured using equipment attached to the TEM, and types and mass % proportion of elements included in a sample were checked through the data.

Embodiment 1: Manufacturing Hydrogen Detecting Sensor

An aqueous solution (about 100 ml) containing copper sulfate (about 0.5M) and sodium thiosulfate (about 0.5 M) was put in a beaker, and thereafter, a flexible plastic substrate (polyethylene terephthalate) cut to a predetermined size was placed to lean slantingly against a wall of the beaker and immersed in the aqueous solution. In order to allow only a sulfide layer to be deposited only on one side of the substrate, the other side of the substrate was marked using a masking tape. A CBD process was performed for about 135 minutes, while maintaining a temperature condition of about 65° C. As a result, a sulfide layer having a thickness of about 50 nm was deposited on the substrate.

After the sulfide layer depositing process was terminated, the sulfide layer was cleaned with water and subsequently dried in the air. Thereafter, a palladium metal catalytic layer having a thickness of about 4 nm was deposited on the sulfide layer at room temperature using an EBD technique as shown in FIG. 1.

Figure 2A:
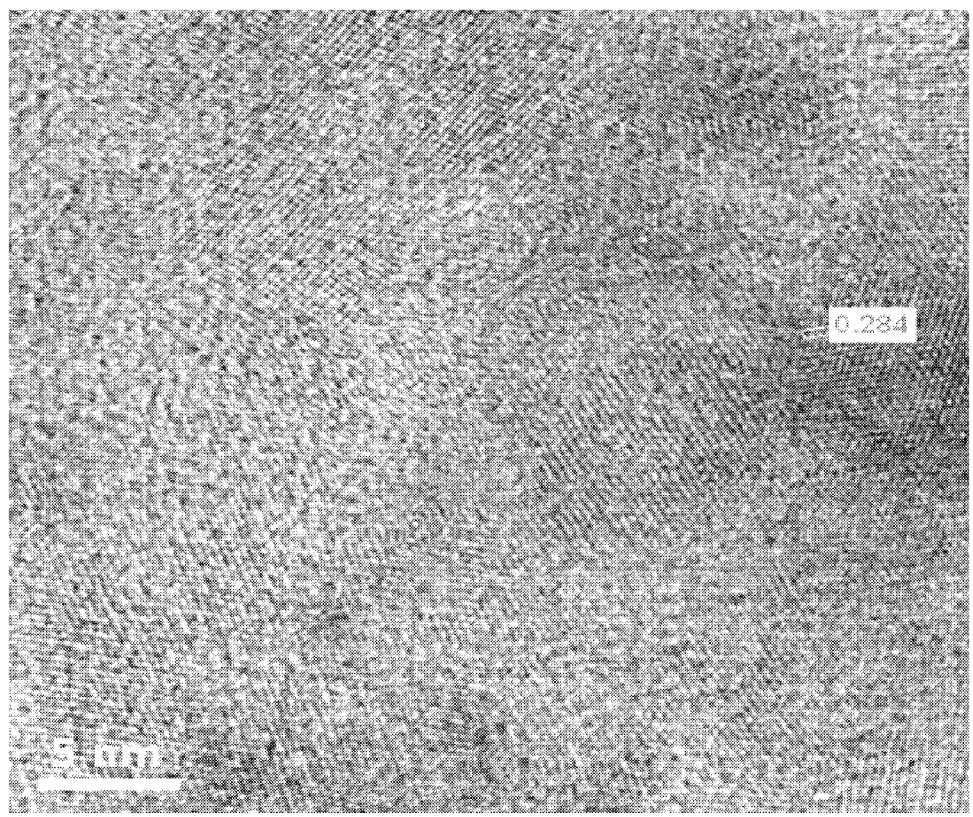
FIG. 2A is a lattice-resolved transmission electron microscopy (TEM) image of a sulfide layer that is included in an exemplary hydrogen detecting sensor manufactured according to an exemplary embodiment of the present invention.
Figure 2B:
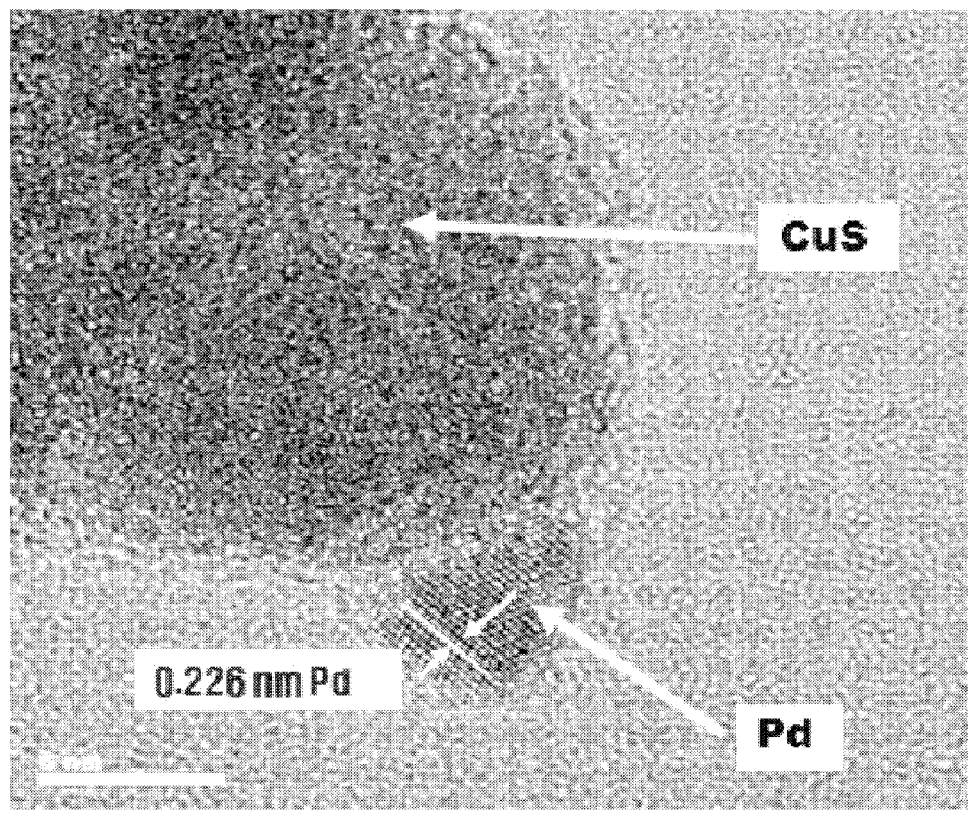
FIG. 2B is a lattice-resolved TEM image of an exemplary metal catalytic layer included in an exemplary hydrogen detecting sensor manufactured according to an exemplary embodiment of the present invention.
Figure 3:
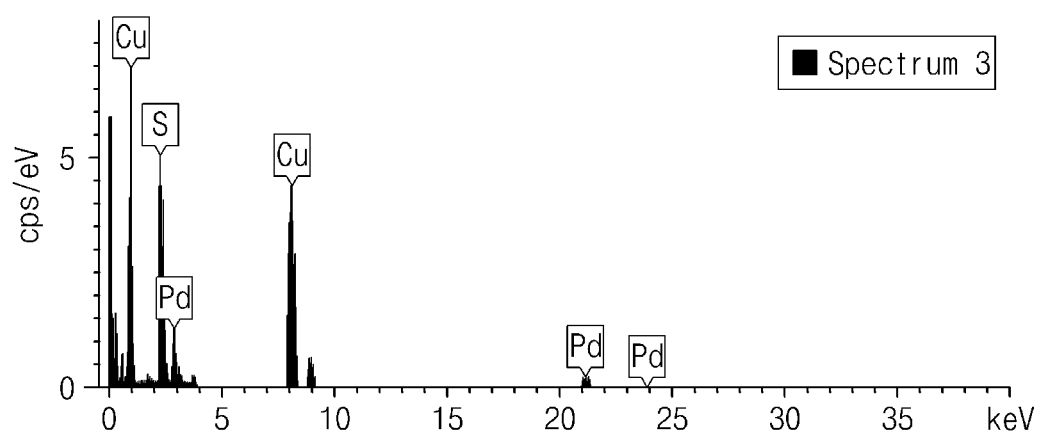
FIG. 3 is an energy-dispersive detector (EDS) spectrum of an exemplary sulfide-layer-metal catalytic layer formed in an exemplary hydrogen detecting sensor manufactured according to an exemplary embodiment of the present invention.

As for the deposited sulfide layer and metal catalytic layer, purity of the sample was measured using a TEM. For instance, a lattice constant of the CuS thin film was about 0.284 nm as shown in FIG. 2A, and lattice constant of the Pd layer was about 0.226 nm as shown in FIG. 2B.

Also, as for an EDS spectrum regarding the CuS—Pd deposition substrate, copper (Cu), sulfur (S), and palladium (Pd) elements were checked as element types and since weight percents of these elements were detected as shown in the following Table 1, it can be confirmed that the Pd layer and the CuS thin film were normally deposited according to the results.

TABLE 1

| Element | K factor | Absorption correction | Wt % | Wt % sigma |
|---|---|---|---|---|
| S | 0.98041 | 1.00 | 27.13 | 0.434 |
| Cu | 1.42103 | 1.00 | 60.01 | 0.78 |
| Pd | 15.66306 | 1.00 | 12.86 | 1.05 |
| Sum | | | 100.00 | |

EXPERIMENTAL EXAMPLES

Experimental Example 1

The hydrogen detecting sensor manufactured in Embodiment 1 was installed in an open chamber with an outlet, and a coloration reaction of the hydrogen detecting sensor, while allowing about 1%(vol/vol) hydrogen (containing about 99%(vol/vol) nitrogen) to pass therethrough under an atmosphere of a mixture of nitrogen, oxygen and vapor, was inspected with naked eyes.

Figure 4:
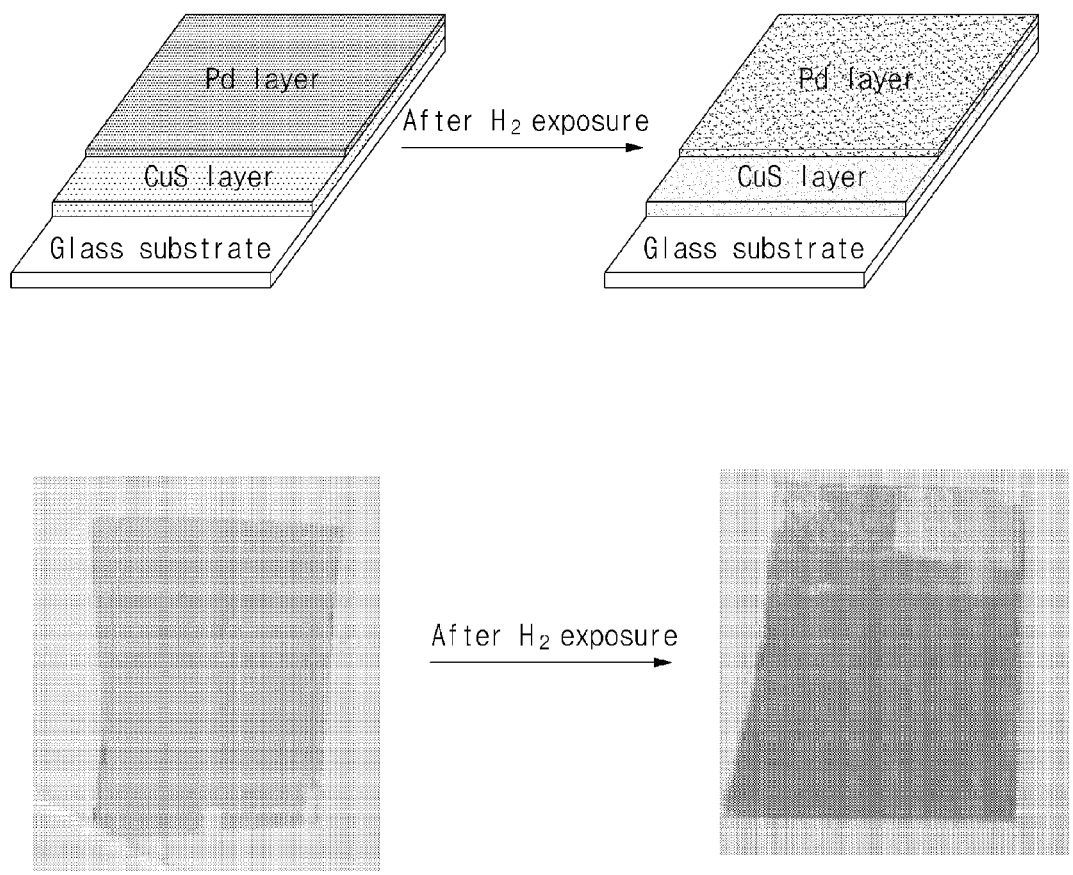
FIG. 4 is a schematic view illustrating an exemplary hydrogen detecting experiment method using an exemplary hydrogen detecting sensor according to experimental example 1 of the present invention.

As a result, the hydrogen detecting sensor, which had a dark green color before being exposed to the hydrogen gas, was changed to have a dark brown color after being exposed to the hydrogen gas as shown in FIG. 4.

Experimental Example 2

Figure 5:
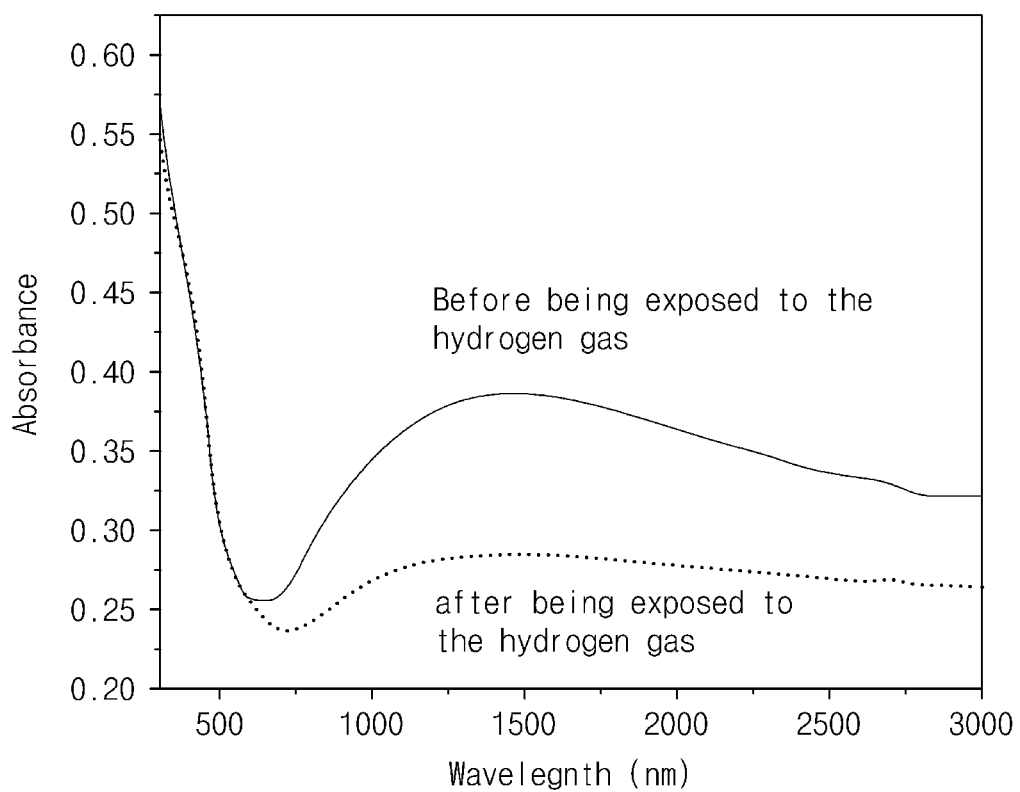
FIG. 5 is a graph illustrating absorbance before and after an exemplary hydrogen detecting sensor manufactured according to an exemplary embodiment of the present invention is exposed to a hydrogen gas.
Figure 6:
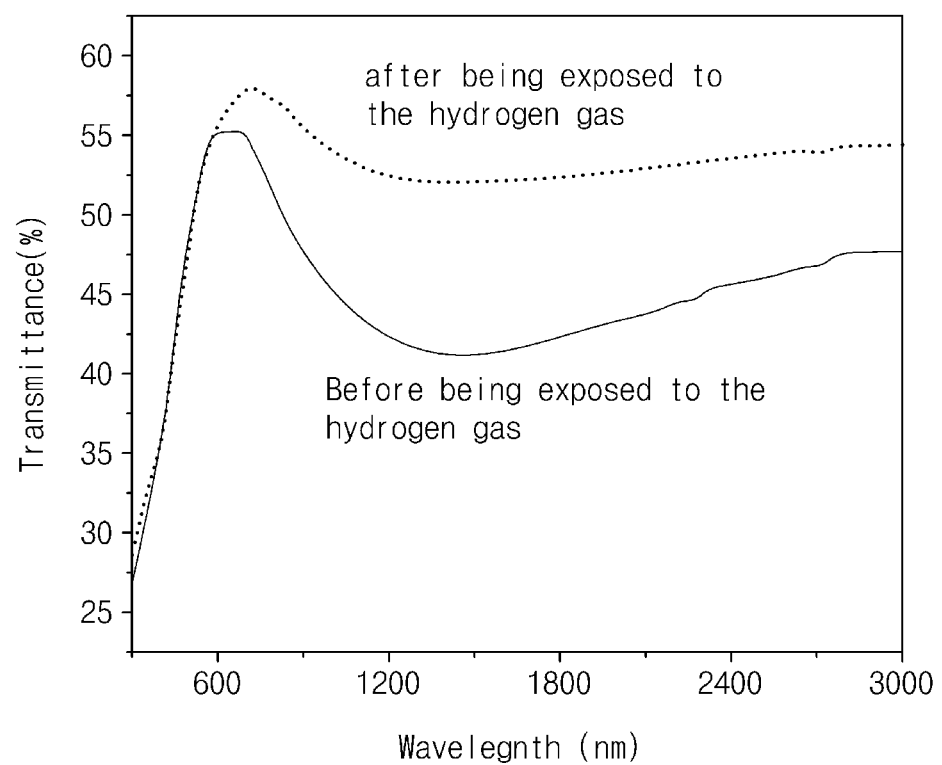
FIG. 6 is a graph illustrating transmittance before and after an exemplary hydrogen detecting sensor manufactured according to an exemplary embodiment of the present invention is exposed to a hydrogen gas.

Reduction of the sulfide layer due to hydrogen gas induced changes in transmittance and absorbance of the hydrogen detecting sensor in an infrared region having a wavelength ranging from about 800 nm to about 3000 nm. FIG. 5 shows an absorption spectrum of the hydrogen detecting sensor in the presence of 100%(vol/vol) hydrogen within a wavelength ranging from about 300 nm to about 3000 nm, and FIG. 6 shows a transmittance spectrum of the hydrogen detecting sensor in the presence of 100%(vol/vol) hydrogen within a wavelength ranging from about 300 nm to about 3000 nm. As shown in FIG. 5, it was observed that after the hydrogen detecting sensor was exposed to the hydrogen gas, absorbance thereof was reduced in the wavelength ranging from about 1100 nm to about 2500 nm, compared with the hydrogen detecting sensor before being exposed to the hydrogen gas. Also, it was observed that after the hydrogen detecting sensor was exposed to the hydrogen gas, transmittance thereof was increased in the wavelength ranging from about 1100 nm to about 2500 nm. Such a change demonstrates sensitivity of the hydrogen detecting sensor of the exemplary embodiment of the present invention with respect to the hydrogen gas.

The hydrogen detecting sensor manufactured according to exemplary embodiments of the present invention may include a sulfide layer that may be reduced by a reaction with a metal catalytic layer and a hydrogen atom, and the reduced sulfide layer may have less corrosion rate with oxygen, moisture, and the like, in the air, and thus, degradation of sensitivity of the hydrogen detecting sensor may be prevented even without an additional protective layer. Also, the hydrogen detecting sensor manufactured according to an exemplary embodiment of the present invention may easily detect low concentration of hydrogen gas concentration of about 1%(vol/vol) or less in the air at room temperature.

The present invention described above may be variously substituted, altered, and modified by those skilled in the art to which the present disclosure pertains without departing from the scope and spirit of the present disclosure. Therefore, the present disclosure is not limited to the above-mentioned exemplary embodiments and the accompanying drawings.

What is claimed is:

1. A hydrogen detecting sensor, comprising
a substrate,
a sulfide layer formed on the substrate and discolored when exposed to hydrogen, and
a metal catalytic layer deposited on the sulfide layer,
wherein the sulfide layer includes one or more sulfides selected from the group comprising of CdS, SnS, MoS, ZnS, SeS, FeS, PdS, and CuS, and
wherein the metal catalytic layer includes one or more of metal particles selected from the group comprising of palladium (Pd) and platinum (Pt).

2. The hydrogen detecting sensor according to claim 1, wherein the sulfide layer is chemically discolored by a chemical reaction with the hydrogen.

3. The hydrogen detecting sensor according to claim 1, wherein the substrate is selected from the group consisting of glass, flexible plastic, silicon, quartz, fused silica, stainless steel, mica, carbon, carbon nano-tube, polymer, ceramic, and porcelain enamel.

4. The hydrogen detecting sensor according to claim 1, wherein the sulfide layer is deposited on the substrate using a chemical bath deposition (CBD) method or a dry deposition method.

5. The hydrogen detecting sensor according to claim 1, wherein the sulfide layer is formed in a thin film by reacting copper sulfate and sodium thiosulfate at a mole ratio of about 1:5 and by bath-depositing.

6. The hydrogen detecting sensor according to claim 1, wherein a thickness of the sulfide layer ranges from about 40 nm to about 50 nm.

7. The hydrogen detecting sensor according to claim 1, wherein the sulfide layer is deposited on the entire region of the substrate such that the substrate is not exposed.

8. The hydrogen detecting sensor according to claim 1, wherein the metal catalytic layer is formed using a hydrothermal method or e-beam evaporation (EBD).

9. The hydrogen detecting sensor according to claim 1, wherein a thickness of the metal catalytic layer ranges from about 4 nm to about 5 nm.

10. The hydrogen detecting sensor according to claim 1, wherein the metal catalytic layer is formed on a portion of the sulfide layer such that at least other portion of the sulfide layer is exposed.

* * * * *